(12) United States Patent
Park et al.

(10) Patent No.: US 8,420,357 B2
(45) Date of Patent: Apr. 16, 2013

(54) RECOMBINANT MICROORGANISM CAPABLE OF PRODUCING POLYLACTATE OR POLYLACTATE COPOLYMER FROM SUCROSE AND METHOD FOR PRODUCING POLYLACTATE OR POLYLACTATE COPOLYMER FROM SUCROSE USING THE SAME

(75) Inventors: Si-Jae Park, Daejeon (KR); Tae-wan Kim, Daejeon (KR); Hye-Ok Kang, Daejeon (KR); Taek-Ho Yang, Daejeon (KR); Sang-Yup Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 230 days.

(21) Appl. No.: 12/676,832

(22) PCT Filed: Aug. 8, 2008

(86) PCT No.: PCT/KR2008/004611
§ 371 (c)(1),
(2), (4) Date: Aug. 9, 2010

(87) PCT Pub. No.: WO2009/031762
PCT Pub. Date: Mar. 12, 2009

(65) Prior Publication Data
US 2011/0008855 A1    Jan. 13, 2011

(30) Foreign Application Priority Data

Sep. 7, 2007  (KR) .................. 10-2007-0091063
Jul. 15, 2008  (KR) .................. 10-2008-0068607

(51) Int. Cl.
*C12P 7/62* (2006.01)
(52) U.S. Cl.
USPC ........................................................ 435/135
(58) Field of Classification Search .................. None
See application file for complete search history.

(56) References Cited

U.S. PATENT DOCUMENTS 6,492,134 B1     12/2002  Aquin et al.
7,169,598 B2      1/2007  Honma et al.
2007/0277268 A1*  11/2007  Cho et al. .................. 800/288

FOREIGN PATENT DOCUMENTS

WO   WO 2006/126796    11/2006

OTHER PUBLICATIONS

Luengo et al., "Bioplastics from Microorganisms", Current Opinion in Microbiology, 2003, pp. 251-260.
Lee, "Bacterial Polyhydroxyalkanoates", Biotechnology and Bioengineering, vol. 49, 1996, pp. 1-14.
Kiechle et al., "Lactate Production by Aerobic Bacteria Grown in Cerebrospinal Fluid", Clinical Chemistry, vol. 30, No. 11, 1984, pp. 1875-1876.
Suriyamongkol et al., "Biotechnological approaches for the production of polyhydroxyalkanoates in microorganisms and plants", Biotechnology Answers 25, 2007, pp. 148-175.
Yu et al., "Polymer blends and composites from renewable resources", Prog. Polym. Sci 31, 2006, pp. 576-602.

* cited by examiner

*Primary Examiner* — Tekchand Saidha
*Assistant Examiner* — Md. Younus Meah
(74) *Attorney, Agent, or Firm* — McKenna Long & Aldridge, LLP

(57) ABSTRACT

Provided are a microorganism capable of producing a polylactate (PLA) or PLA copolymer from sucrose and a method of producing the PLA or PLA copolymer from sucrose using the same. A gene of an enzyme converting lactate into lactyl-CoA and a gene of a polyhydroxyalkanoate (PHA) synthase using lactyl-CoA as a substrate are introduced into a microorganism capable of using sucrose as a substrate, and the microorganism is cultured using sucrose as the substrate, thereby allowing efficient production of a PLA or PLA copolymer.

14 Claims, 1 Drawing Sheet

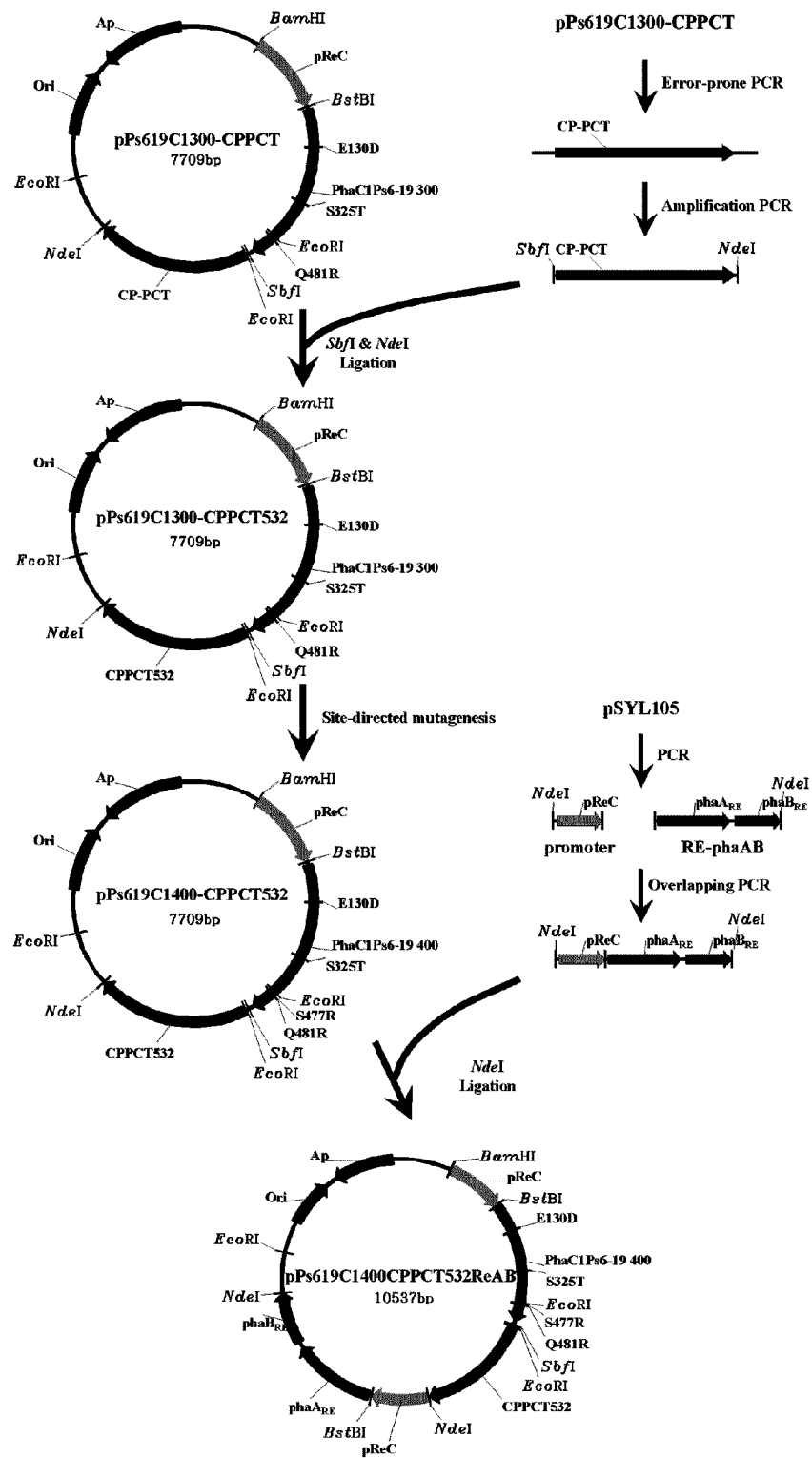

US 8,420,357 B2

RECOMBINANT MICROORGANISM CAPABLE OF PRODUCING POLYLACTATE OR POLYLACTATE COPOLYMER FROM SUCROSE AND METHOD FOR PRODUCING POLYLACTATE OR POLYLACTATE COPOLYMER FROM SUCROSE USING THE SAME

This application claims the benefit of PCT/KR2008/004611 filed on Aug. 8, 2008, Korean Patent Application No. 10-2007-0091063 filed on Sep. 7, 2007, and Korean Patent Application No. 10-2008-0068607 filed on Jul. 15, 2008, all of which are hereby incorporated herein by reference for all purposes in their entirety.

TECHNICAL FIELD

The present invention relates to a recombinant microorganism capable of producing a polylactate (PLA) or PLA copolymer from sucrose and a method of producing a PLA or PLA copolymer from sucrose using the microorganism.

BACKGROUND ART

Polylactate (PLA) is a typical biodegradable polymer derived from lactate that is highly applicable commercially and biomedically. Although preparation of PLA presently involves polymerization of lactate produced by fermenting microorganisms, only PLA with a low molecular weight of about 1000 to 5000 daltons is obtained by direct polymerization of lactate. In order to synthesize PLA with a molecular weight of 100,000 daltons or higher, PLA with a low molecular weight obtained by direct polymerization of lactate may be polymerized using a chain coupling agent. In this method, however, the entire process becomes complicated due to addition of an organic solvent or the chain coupling agent, which are not easy to remove. A presently commercially available process of preparing high-molecular weight PLA may include converting lactate into lactide and synthesizing PLA using ring-opening polycondensation of lactide rings.

When PLA is synthesized by chemical synthesis of lactate, a PLA homopolymer is easily obtained, but a PLA copolymer composed of various types of monomers is difficult to synthesize and commercially unavailable.

Meanwhile, polyhydroxyalkanoate (PHA) is polyester stored by microorganisms as energy or a carbon source when there are excessive carbon sources and a lack of other nutrients such as phosphorus (P), nitrogen (N), magnesium (Mg), and oxygen (O), etc. Since PHA has similar physical properties to conventional synthetic polymers from petroleum and exhibits complete biodegradability, it is being recognized as a substitute for conventional synthetic plastics.

In order to produce PHAs using microorganisms, enzymes converting microbial metabolic products into a PHA monomer and a PHA synthase for synthesizing a PHA polymer using the PHA monomer are needed. When synthesizing PLA and PLA copolymer using microorganisms, the same system is required, and enzymes for providing lactyl-CoA are needed in addition to an enzyme for providing hydroxyacyl-CoA, which is an original substrate of a PHA synthase.

Furthermore, it is very important to adopt a low-cost substrate in order to economically produce biodegradable polymers. In particular, it is necessary to develop a technique of producing a PLA or PLA copolymer using sucrose as a low-cost substrate.

DISCLOSURE

Technical Problem

The present invention is directed to a microorganism capable of producing a polylactate (PLA) or PLA copolymer using sucrose as a substrate and a method of producing a PLA or PLA copolymer using the same.

Technical Solution

One aspect of the present invention provides a method of producing a polylactate (PLA) or hydroxyalkanoate-lactate copolymer from sucrose. The method includes culturing or growing a cell or plant in an environment containing lactate and sucrose or an environment containing lactate, sucrose, and hydroxyalkanoate. The cell or plant contains a gene of an enzyme converting lactate into lactyl-CoA and a gene of a polyhydroxyalkanoate (PHA) synthase using lactyl-CoA as a substrate and is able to produce a PLA or hydroxyalkanoate-lactate copolymer using sucrose as a substrate. Thereafter, the PLA or hydroxyalkanoate-lactate copolymer is retrieved from the cell or plant.

The present inventors successfully synthesized PLA and PLA copolymer using a propionyl-CoA transferase from *Clostridium propionicum* for providing lactyl-CoA, and a mutant of a PHA synthase from *Pseudomonas* sp. 6-19 using lactyl-CoA as a substrate, as disclosed in Korean Patent Application No. 10-2006-0116234.

Furthermore, the present inventors attempted to produce PLA and PLA copolymer using a low-cost substrate, sucrose, in order to economically produce biodegradable polymers. As a result, the present inventors transformed *E. coli* using sucrose as a low-cost substrate with a plasmid expressing a propionyl-CoA transferase from *Clostridium propionicum* and a PHA synthase from *Pseudomonas* sp. 6-19, and found that PLA and PLA copolymer could be efficiently produced from sucrose using the transformed recombinant *E. coli*. This led them to complete the present invention.

The cell or plant capable of producing the PLA or PLA copolymer (hydroxyalkanoate-lactate copolymer) may be obtained by transforming a cell or plant that does not include at least one of: (a) the gene of the enzyme converting lactate into lactyl-CoA and (b) the gene of the PHA synthase using lactyl-CoA as the substrate with at least one of (a) and (b). That is, the cell or plant capable of producing the PLA or hydroxyalkanoate-lactate copolymer may be obtained by transforming a cell or plant not having (a) and (b) with at least one of (a) and (b), or by transforming a cell or plant not having (a) but having (b) with (a), but the present invention is not limited thereto. For example, according to the present invention, when a cell has one of (a) and (b), the cell capable of producing the PLA or hydroxyalkanoate-lactate copolymer may be obtained by amplifying the included one of (a) and (b) and transforming the cell with the absent one of (a) and (b).

In the present invention, hydroxyalkanoate of the hydroxyalkanoate-lactate copolymer may be at least one selected from the group consisting of 3-hydroxybutyrate, 3-hydroxyvalerate, 4-hydroxybutyrate, medium chain-length (D)-3-hydroxycarboxylic acid with 6 to 14 carbon atoms, 2-hydroxypropionic acid, 3-hydroxypropionic acid, 3-hydroxyhexanoic acid, 3-hydroxyheptanoic acid, 3-hydroxyoctanoic acid, 3-hydroxynonanoic acid, 3-hydroxydecanoic acid, 3-hydroxyundecanoic acid, 3-hydroxydodecanoic acid, 3-hydroxytetradecanoic acid, 3-hydroxyhexadecanoic acid, 4-hydroxyvaleric acid, 4-hydroxyhexanoic acid, 4-hydroxyheptanoic acid, 4-hydroxyoctanoic acid, 4-hydroxydecanoic acid, 5-hydroxyvaleric acid, 5-hydroxyhexanoic acid, 6-hydroxydodecanoic acid, 3-hydroxy-4-pentenoic acid, 3-hydroxy-4-trans-hexenoic acid, 3-hydroxy-4-cis-hexenoic acid, 3-hydroxy-5-hexenoic acid, 3-hydroxy-6-trans-octenoic acid, 3-hydroxy-6-cis-octenoic acid, 3-hydroxy-7-octenoic acid, 3-hydroxy-8-nonenoic acid, 3-hydroxy-9-decenoic acid, 3-hydroxy-5-cis-dodecenoic acid, 3-hydroxy-6-cis-dodecenoic acid, 3-hydroxy-5-cis-tetradecenoic acid, 3-hydroxy-7-cis-tetradecenoic acid, 3-hydroxy-5,8-cis-cis-tetradecenoic acid, 3-hydroxy-4-methylvaleric acid, 3-hydroxy-4-methylhexanoic acid, 3-hydroxy-5-methylhexanoic acid, 3-hydroxy-6-methylheptanoic acid, 3-hydroxy-4-methyloctanoic acid, 3-hydroxy-5-methyloctanoic acid, 3-hydroxy-6-methyloctanoic acid, 3-hydroxy-7-methyloctanoic acid, 3-hydroxy-6-methylnonanoic acid, 3-hydroxy-7-methylnonanoic acid, 3-hydroxy-8-methylnonanoic acid, 3-hydroxy-7-methyldecanoic acid, 3-hydroxy-9-methyldecanoic acid, 3-hydroxy-7-methyl-6-octenoic acid, malic acid, 3-hydroxysuccinic acid-methylester, 3-hydroxyadipinic acid-methylester, 3-hydroxysuberic acid-methylester, 3-hydroxyazelaic acid-methylester, 3-hydroxysebacic acid-methylester, 3-hydroxysuberic acid-ethylester, 3-hydroxysebacic acid-ethylester, 3-hydroxypimelic acid-propylester, 3-hydroxysebacic acid-benzylester, 3-hydroxy-8-acetoxyoctanoic acid, 3-hydroxy-9-acetoxynonanoic acid, phenoxy-3-hydroxybutyric acid, phenoxy-3-hydroxyvaleric acid, phenoxy-3-hydroxyheptanoic acid, phenoxy-3-hydroxyoctanoic acid, para-cyanophenoxy-3-hydroxybutyric acid, para-cyanophenoxy-3-hydroxyvaleric acid, para-cyanophenoxy-3-hydroxyhexanoic acid, para-nitrophenoxy-3-hydroxyhexanoic acid, 3-hydroxy-5-phenylvaleric acid, 3-hydroxy-5-cyclohexylbutyric acid, 3,12-dihydroxydodecanoic acid, 3,8-dihydroxy-5-cis-tetradecenoic acid, 3-hydroxy-4,5-epoxydecanoic acid, 3-hydroxy-6,7-epoxydodecanoic acid, 3-hydroxy-8,9-epoxy-5,6-cis-tetradecanoic acid, 7-cyano-3-hydroxyheptanoic acid, 9-cyano-3-hydroxynonanoic acid, 3-hydroxy-7-fluoroheptanoic acid, 3-hydroxy-9-fluorononanoic acid, 3-hydroxy-6-chlorohexanoic acid, 3-hydroxy-8-chlorooctanoic acid, 3-hydroxy-6-bromohexanoic acid, 3-hydroxy-8-bromooctanoic acid, 3-hydroxy-11-bromoundecanoic acid, 3-hydroxy-2-butenoic acid, 6-hydroxy-3-dodecenoic acid, 3-hydroxy-2-methylbutyric acid, 3-hydroxy-2-methylvaleric acid, and 3-hydroxy-2,6-dimethyl-5-heptenoic acid, but the present invention is not limited thereto.

In the present invention, the gene of the enzyme converting lactate into lactyl-CoA may be a propionyl-CoA transferase (pct) gene. More specifically, the gene of the enzyme converting lactate into lactyl-CoA may be a pct gene from *Clostridium propionicum*. In a specific example of the present invention, the gene of the enzyme converting lactate into lactyl-CoA may have one selected from the group consisting of: a base sequence (CpPCT) of SEQ ID NO: 1; a base sequence (CpPCT522) obtained by mutating T78C, T669C, A1125G and T1158C in the base sequence of SEQ ID NO:1; a base sequence (CpPCT512) obtained by mutating A1200G in the base sequence of SEQ ID NO:1; a base sequence (CpPCT531) obtained by mutating A1200G in the base sequence of SEQ ID NO:1 and mutating Gly335Asp in an amino-acid sequence of SEQ ID NO: 2; a base sequence (CpPCT533) obtained by mutating T669C, A1125G and T1158Ca in the base sequence of SEQ ID NO:1 and mutating Asp65Gly in the amino-acid sequence of SEQ ID NO: 2; a base sequence (CpPCT535) obtained by mutating T669C, A1125G, and T1158C in the base sequence of SEQ ID NO: 1 and mutating Asp65Asn in the amino-acid sequence of SEQ ID NO: 2; a base sequence (CpPCT537) obtained by mutating T669C, A1125G, and T1158C in the base sequence of SEQ ID NO: 1 and mutating Thr199Ile in the amino-acid sequence of SEQ ID NO: 2; a base sequence (CpPCT532) obtained by mutating A1200G in the base sequence of SEQ ID NO: 1 and mutating Ala243Thr in the amino-acid sequence of SEQ ID NO: 2; a base sequence (CpPCT534) obtained by mutating A1200G in the base sequence of SEQ ID NO: 1 and mutating Asp257Asn in the amino-acid sequence of SEQ ID NO: 2; and a base sequence (CpPCT540) obtained by mutating T78C, T669C, A1125G and T1158C in the base sequence of SEQ ID NO: 1 and mutating Val193Ala in the amino-acid sequence of SEQ ID NO: 2.

In particular, the CpPCT532 gene may be a mutant gene of a propionyl-CoA transferase from *Clostridium propionicum* that is preferable for producing a PLA or PLA copolymer using sucrose.

The cell or plant according to the present invention may include the gene of the PHA synthase using lactyl-CoA as the substrate, which is a gene of a PHA synthase from *Pseudomonas* sp. 6-19. The gene of the PHA synthase using lactyl-CoA as the substrate may be a gene having an amino-acid sequence of SEQ ID NO: 4 or a gene having a base sequence corresponding to a mutant amino acid sequence in which at least one selected from the group consisting of E130D, S325T, S477R, S477H, S477F, S477Y, S477G, Q481M, Q481K, and Q481R is mutated in the amino-acid sequence of SEQ ID NO: 4.

In particular, the phaC1$_{Ps6-19}$400 gene may be the gene of a PHA synthase from *Pseudomonas* sp. 6-19 that is preferable for producing the PLA or PLA copolymer using sucrose.

Also, the cell or plant according to the present invention may further include a gene of an enzyme for producing hydroxyacyl-CoA from sucrose. Since a recombinant cell or plant further including the gene of the enzyme for producing hydroxyacyl-CoA from sucrose can produce hydroxyacyl-CoA on its own, even if hydroxyalkanoate is not included in a medium, hydroxyalkanoate-lactate copolymer may be produced with high yield. In a specific example of the present invention, the enzymes for producing hydroxyacyl-CoA from sucrose may be a ketothiolase and an acetoacetyl-CoA reductase, but the present invention is not limited thereto. The ketothiolase and acetoacetyl-CoA reductase may be derived from *Ralstonia eutropha*.

In a specific example of the present invention, the cell capable of producing the PLA or hydroxyalkanoate-lactate copolymer may be a bacterium, particularly, *E. coli*.

The present invention provides a cell or plant that is transformed with a recombinant vector for producing a PLA or PLA copolymer containing a gene of an enzyme converting lactate into lactyl-CoA and a gene of a polyhydroxyalkanoate (PHA) synthase using lactyl-CoA as a substrate and uses sucrose as a substrate. The cell or plant may further include a gene of an enzyme for producing 3-hydroxybutyl-CoA from sucrose.

A vector refers to a DNA construct containing a DNA sequence operably linked to a suitable control sequence capable of expressing DNA in an appropriate host. In the present invention, the vector may be a plasmid vector, a bacteriophage vector, a cosmid vector, or a yeast artificial chromosome (YAC) vector. For the purpose of the present invention, a plasmid vector may be used. A typical plasmid vector that serves the purpose of the invention includes (a) a replication origin that allows efficient replication such that each host cell includes several hundred plasmid vectors, (b) an antibiotic-resistance gene that allows selection of a host cell transformed into a plasmid vector, and (c) a restriction enzyme cleavage site in which a foreign DNA fragment may be inserted. Even if there is no appropriate restriction enzyme cleavage site, a vector may be easily ligated with foreign DNA by an ordinary method using a synthetic oligonucleotide adaptor or a linker.

After the ligation process, the vector has to be transformed into an appropriate host cell. In the present invention, the host cell may be a prokaryotic cell or a eukaryotic cell. Preferably, the host cell is a prokaryotic cell. The prokaryotic cell may be a microorganism having one of the above-described three genes or a microorganism having none of the above-described three genes, for example, E. coli. The E. coli may include E. coli strain DH5a, E. coli strain JM101, E. coli K12, E. coli W3110, E. coli X1776, E. coli XL1-Blue (Stratagene), E. coli B, etc. However, E. coli strains, such as FMB101, NM522, NM538, and NM539, and other prokaryotic species and genera may be also used. In addition to the above-described E. coli and microorganisms having genes of the PHA synthase, Agrobacterium sp. strains such as Agrobacterium A4, bacilli such as Bacillus subtilis, and other enterobacteria such as Salmonella typhimurium or Serratia marcescens, may be used as host cells. Known eukaryotic host cells such as yeast and mold, insect cells such as spodoptera frugiperda (SF9), animal cells such as Chinese hamster ovary (CHO) cells and mouse cells, and tissue-cultured human and plant cells may be used as host cells. When the vector is transformed into an appropriate host, the vector is capable of replicating or functioning irrespective of a host genome or, in some cases, being integrated with the genome itself.

As is known to one skilled in the art, in order to raise an expression level of a transformed gene in a host cell, the transformed gene must be operably linked to an expression control sequence that performs transcription and translation functions in a selected expression host. Preferably, the expression control sequence and the transformed gene are included in a single expression vector including both a bacterial selectable marker and a replication origin. When an expression host is a eukaryotic cell, the expression vector must further include an expression marker that is useful in the eukaryotic expression host.

The term "expression control sequence" means a DNA sequence essential for expression of an operably linked coding sequence in a specific host. The control sequence includes a promoter required for transcription, an arbitrary operator sequence for controlling the transcription, a sequence for encoding an appropriate mRNA ribosome binding site (RBS), and a sequence for controlling termination of transcription and translation. For example, a control sequence suitable for a prokaryote includes a promoter, a random operator sequence, and an RBS. A control sequence suitable for a eukaryotic cell includes a promoter, a polyadenylation signal, and an enhancer. The most important factor that affects the expression amount of a gene in a plasmid is a promoter. A SRα promoter or a cytomegalovirus promoter may be used as a high-expression promoter.

In order to express a DNA sequence of the present invention, any one of various expression control sequences may be used for a vector. The expression control sequence may be, for example, early and late promoters of SV40 or adenovirus, the lac system, the trp system, the tac system, the trc system, T3 and T7 promoters, the major operator and promoter regions of phage λ, the control region of fd code protein, the promoters of 3-phosphoglycerate kinase or other glycolytic enzymes, the promoters of phosphatase, for example, the promoters, e.g., Pho5, the promoter of a yeast α-mating system, other sequences with configurations or derivations known to control expression of a prokaryotic or eukaryotic cell or their viruses, and various combinations thereof.

When a nucleic acid is disposed in a functional relationship with another nucleic acid sequence, it is operably linked to the nucleic acid sequence. An appropriate molecule (e.g., a transcription-activating protein) may be a gene and control sequence(s) that are linked in such a manner as to enable expression of the gene when it couple with the control sequence(s). For example, DNA of a pre-sequence or a secretory leader is operably linked to DNA of polypeptide when it is expressed as a pre-protein that participates in secretion of polypeptide; a promoter or enhancer is operably linked to a coding sequence when it affects transcription of the coding sequence; an RBS is operably linked to a coding sequence when it affects transcription of the coding sequence; or the RBS is operably linked to the coding sequence when it is disposed to facilitate translation. In general, "operably linked sequences" means that DNA sequences being linked are contiguous, and in case of the secretory leader contiguous and in a reading frame. However, an enhancer does not have to contact a coding sequence. Linkage between sequences may be performed by ligation in a convenient restriction enzyme site. However, when there is no restriction enzyme site, a synthetic oligonucleotide adaptor or a linker may be used according to an ordinary method.

Of course, it should be understood that all vectors and expression control sequences do not equally function to express DNA sequences according to the present invention. Similarly, all hosts do not equally function with respect to the same expression system. However, one skilled in the art may appropriately select from among various vectors, expression control sequences, and hosts without either departing from the scope of the present invention or bearing excessive experimental burden. For example, a vector must be selected considering a host because the vector must be replicated in the host. Specifically, the copy number and copy number control of the vector and expression of other protein (e.g., an antibiotic marker) encoded by the corresponding vector must be also considered. One skilled in the art may select an appropriate combination out of various vectors, expression control sequences, and hosts within appropriate ranges of the above-described variables.

Also, the transformation of a eukaryotic cell may be easily accomplished using a calcium chloride method described in section 1.82, supra by Sambrook et al. Alternatively, electroporation may be employed for transformation of these cells (Neumann et al., EMBO J., 1:841 (1982)).

Meanwhile, transformation of a plant may be achieved by an ordinary method using Agrobacterium, a virus vector, etc. For example, a microorganism is transformed with a recombinant vector containing a gene according to the present invention, and the transformed Agrobacterium sp. microorganism may infect tissue of a target plant, thereby obtaining a transformed plant. For instance, a transformed plant according to the present invention may be obtained in the same manner as or in a similar manner to a method of producing PHA using a transformed plant disclosed in WO 94/11519 or U.S. Pat. No. 6,103,956. More specifically, production of a transfected plant may involve (a) pre-culturing an explant of a target plant and co-culturing the explant with transformed agrobacterium for transfection of the plant; (b) culturing the transfected explant in a callus-inducing medium to obtain a callus; and (c) cleaving the callus and culturing the cleaved callus in a shoot-inducing medium to obtain a shoot.

In the present invention, the term "explant" refers to a tissue fragment cut off from a plant and includes a cotyledon or a hypocotyl. The cotyledon or hypocotyl may be used as an explant of a plant used for the method of the present invention. The cotyledon, which is obtained by disinfecting and cleaning a seed of a plant and germinating the seed in a Murashige and Skoog (MS) medium, is preferably used.

In the present invention, target plants to be transformed may be tobacco, tomatoes, red peppers, beans, rice plants, corn, etc, but the present invention is not limited thereto. Also, it is known to one skilled in the art that even if a plant used for transformation is sexually reproducible, it can be asexually reproduced by tissue culture, etc.

Advantageous Effects

As explained above, the present invention provides a cell or plant capable of efficiently producing a polylactate (PLA) or PLA copolymer from sucrose and a method of producing PLA and PLA copolymer by growing or culturing the cell or plant.

DESCRIPTION OF DRAWINGS

FIG. 1 is a schematic diagram of a process of preparing a recombinant expression vector containing a mutant gene of a polyhydroxyalkanoate (PHA) synthase from *Pseudomonas* sp. 6-19, a mutant gene of a propionyl-CoA transferase from *Clostridium propionicum*, and a gene of a phaAB from *Ralstonia eutropha* according to an example of the present invention.

MODES OF THE INVENTION

Hereinafter, examples of the present invention will be described in detail. However, the present invention is not limited to the examples disclosed below, but can be implemented in various modified forms. The present examples are provided to fully enable those of ordinary skill in the art to embody and practice the invention Example 1

Preparation of a Recombinant *E. Coli*

A recombinant *E. coli* W transformed with a pPs619C1400CPPCT532ReAB plasmid was prepared. The *E. coli* strain W (ATCC9637) according to the present Example may metabolize sucrose as a carbon source.

The pPs619C1400CPPCT532ReAB plasmid prepared for the present invention was constructed to express four kinds of major enzymes. The major enzymes are essential for biosynthesis of poly(3-hydroxybutyrate-co-lactate), which is a biodegradable polymer, in the *E. coli*. The major enzymes may be phaC1$_{Ps6-19}$400, which is a polymerase from *Pseudomonas* sp. 6-19 (KCTC 11027BP), a propionyl-CoA transferase from *Clostridium propionicum* (CP-PCT), which is an enzyme transferring CoA from acetyl-CoA to lactate to be converted into lactyl-CoA, and a ketothiolase(phaA$_{RE}$) and an acetoacetyl-CoA reductase (phaB$_{RE}$) from *Ralstonia eutropha*, which are enzymes for synthesizing 3-hydroxybutyl-CoA from sucrose. The pPs619C1400CPPCT532ReAB plasmid includes phaC1$_{Ps6-19}$400, CPPCT532, phaA$_{RE}$ and phaB$_{RE}$ genes respectively encoding the above major enzymes (refer to FIG. 1).

Also, the phaC1Ps6-19400 and CPPCT532 genes are respectively obtained by mutating a gene of phaC1$_{Ps6-19}$, which is a PHA synthase from *Pseudomonas* sp. of SEQ ID NO: 3, and a gene of a CP-PCT of SEQ ID NO: 1, to be advantageous for PLA and PLA copolymer. The pPs619C1400CPPCT532ReAB plasmid is prepared to constitutively express all four genes in the recombinant *E. coli*.

Example 1-1

Preparation of a Substrate-Specific Mutant of a PHA Synthase from *Pseudomonas* Sp. 6-19

Among various kinds of PHA synthases, a Type II PHA synthase is known as a medium-chain-length PHA (MCL-PHA) synthase for polymerizing a substrate having relatively many carbon atoms, and the MCL-PHA synthase is expected to be very useful in production of a PLA copolymer. Although a phaC1 synthase from *Pseudomonas* sp. 61-3, which has a high homology with the phaC1$_{Ps6-19}$ synthase obtained according to the present invention, is the Type II synthase, it has been reported that the phaC 1 synthase has a relatively wide range of substrate specificity (Matsusaki et al., J. *Bacteria.*, 180:6459, 1998), and results of research into a mutant suitable for production of short-chain-length PHA (SCL-PHA) were reported (Takase et al., *Biomacromolecules*, 5:480, 2004). Based on the above research, the present inventors prepared mutants of a phaC1$_{Ps6-19}$ synthase by an SDM method using amino acids affecting SCL activation, as disclosed in Korean Patent Application No. 10-2006-0116234.

More specifically, in order to separate a PHA synthase ((phaC1$_{Ps6-19}$) gene from *Pseudomonas* sp. 6-19(KCTC 11027BP), the total DNA of *Pseudomonas* sp. 6-19 was extracted, primers having base sequences of SEQ ID NOs: 5 and 6 were prepared based on the phaC1$_{Ps6-19}$ base sequence (Ae-jin Song, Master's Thesis, Department of Chemical and Biomolecular Engineering, KAIST, 2004), and polymerase chain reaction (PCR) was performed to obtain the phaC1$_{Ps6-19}$ gene.

```
SEQ ID NO: 5: 5'-GAG AGA CAA TCA AAT CAT GAG TAA
CAA GAG TAA CG-3'

SEQ ID NO: 6: 5'-CAC TCA TGC AAG CGT CAC CGT TCG
TGC ACG TAC-3'
```

When Agarose gel electrophoresis was performed on a PCR reactant, a 1.7-kbp gene fragment corresponding to the phaC1$_{Ps6-19}$ gene was confirmed. In order to express the phaC1$_{Ps6-19}$ synthase, an operon-type constitutive expression system in which a monomer supplying enzyme and a synthase are expressed together was adopted.

From a pSYL105 vector (Lee et al., *Biotech. Bioeng.*, 1994, 44:1337-1347), a DNA fragment containing a PHB producing operon from *Ralstonia eutropha* H16 was cleaved with BamHI/EcoRI, and then inserted into a BamHI/EcoRI restriction site of pBluescript II (Stratagene), thereby preparing a pReCAB recombinant vector.

It is known that the pReCAB vector constitutively expresses a PHA synthase (phaC$_{RE}$) and monomer-supplying enzymes (phaA$_{RE}$ and phaB$_R$) by a PHB operon promoter, and also effectively operated in *E. coli* (Lee et al., *Biotech. Bioeng.*, 1994, 44:1337-1347). The pReCAB vector was cleaved with BstBI/SbfI to remove a *R. eutropha* H16 PHA synthase (phaC$_{RE}$), and the phaC1$_{Ps6-19}$ gene was inserted into a BstBI/SbfI restriction site, thereby preparing a pPs619C1-ReAB recombinant vector.

In order to prepare a phaC1$_{Ps6-19}$ synthase gene fragment having only a BstBI/SbfI restriction site at an either end, an endogenous BstBI site was removed by site-directed mutagenesis (SDM) without changes of amino acids, and the BstBI/SbfI restriction site was added by overlapping PCR using primers having base sequences of SEQ ID NOs: 7 and 8, 9 and 10, and 11 and 12.

```
SEQ ID NO: 7: 5'-atg ccc gga gcc ggt tcg aa-3'

SEQ ID NO: 8: 5'-CGT TAC TCT TGT TAC TCA TGA TTT
GAT TGT CTC TC-3'

SEQ ID NO: 9: 5'-GAG AGA CAA TCA AAT CAT GAG TAA
CAA GAG TAA CG-3'

SEQ ID NO: 10: 5'-CAC TCA TGC AAG CGT CAC CGT TCG
TGC ACG TAC-3'

SEQ ID NO: 11: 5'-GTA CGT GCA CGA ACG GTG ACG CTT
GCA TGA GTG-3'

SEQ ID NO: 12: 5'-aac ggg agg gaa cct gca gg-3'
```

The sequence of the phaC1$_{Ps6-19}$ gene of the prepared pPs619C1-ReAB recombinant vector was confirmed by sequencing and represented as SEQ ID NO: 3, and a sequence of an amino acid encoded by the base sequence of SEQ ID NO: 3 was represented as SEQ ID NO: 4.

In order to check if the phaC1$_{Ps6-19}$ synthase produces PHB or not, the pPs619C1-ReAB recombinant vector was transformed into *E. coli* XL-1Blue(Stratagene), and then the transformed *E. coli* was grown in a PHB detection medium (Luria Bertani (LB) agar, glucose 20 g/L, Nile red 0.5 μg/ml). As a result, PHB production was not detected. Three amino-acid sites affecting SCL activity were found via amino-acid sequence analysis, and mutants of a phaC1$_{Ps6-19}$ synthase were prepared by SDM using primers of SEQ ID NOs: 13 to 18 as shown in Table 1.

TABLE 1

| Recombinant vector | Nucleic acid substitution | Amino acid substitution | Primer |
|---|---|---|---|
| pPs619C1200-ReAB | AGC →ACC | S325T | SEQ ID NOs: 13/14 |
|  | CAG →ATG | Q481M | SEQ ID NOs: 15/16 |
| pPs619C1300-ReAB | GAA →GAT | E130D | SEQ ID NOs: 17/18 |
|  | AGC →ACC | S325T | SEQ ID NOs: 13/14 |
|  | CAG →ATG | Q481M | SEQ ID NOs: 15/16 |

```
S325T
SEQ ID NO: 13: 5'-CTG ACC TTG CTG GTG ACC GTG CTT GAT ACC ACC-3'
SEQ ID NO: 14: 5'-GGT GGT ATC AAG CAC GGT CAC CAG CAA GGT CAG-3'
Q481M
SEQ ID NO: 15: 5'-CGA GCA GCG GGC ATA TC A TGA GCA TCC TGA ACC CGC-3'
SEQ ID NO: 16: 5'-GCG GGT TCA GGA TGC TCA TGA TAT GCC CGC TGC TCG-3'
E130D
SEQ ID NO: 17: 5'-atc aac ctc atg acc gat gcg atg gcg ccg acc-3'
SEQ ID NO: 18: 5'-ggt cgg cgc cat cgc atc ggt cat gag gtt gat-3'
```

The recombinant vectors were transformed into *E. coli* XL-1Blue and grown in a PHB detection medium (LB agar, glucose 20 g/L, Nile red 0.5 μg/ml). As a result, production of PHB could be confirmed in both *E. coli* XL-1Blue transformed with pPs619C1200-ReAB and *E. coli* XL-1Blue transformed with pPs619C1300-ReAB. That is, 3HB-CoA was produced from glucose due to monomer-supplying enzymes, phaA$_{RE}$ and phaB$_{RE}$, and phaC1$_{Ps6-19}$ synthase SCL mutants (phaC1$_{Ps6-19}$200 & phaC1$_{Ps6-19}$300) synthesized PHB using 3HB-CoA as a substrate.

Here, in order to construct an operon-type constitutive expression system expressing a propionyl-CoA transferase from *Clostridium propionicum* (CP-PCT) for providing lactyl-CoA functioning as a monomer required for synthesis of PLA and PLA copolymer, a cp-pct gene was used. For the cp-pct gene, a DNA fragment obtained by polymerizing chromosomal DNA of *Clostridium propionicum* was cloned by PCR using primers of SEQ ID NOs: 19 and 20. In this case, an NdeI site existing in a wild-type cp-pct gene was removed by SDM to facilitate cloning.

```
SEQ ID NO: 19: 5'-
ggaattcATGAGAAAGGTTCCCATTATTACCGCAGATGA

SEQ ID NO: 20: 5'-gc tctaga tta gga ctt cat
ttc ctt cag acc cat taa gcc ttc tg
```

Also, overlapping PCR was performed using primers of SEQ ID NOs: 21 and 22 in order to add a SbfI/NdeI restriction site.

```
SEQ ID NO: 21: 5'-agg cct gca ggc gga taa caa ttt
cac aca gg-3'

SEQ ID NO: 22: 5'-gcc cat atg tct aga tta gga ctt
cat ttc c-3'
```

A pPs619C1300-ReAB vector containing phaC1$_{Ps6-19}$300, which is a phaC1$_{Ps6-19}$ synthase SCL mutant, was cleaved with SbfI/NdeI to remove the monomer-supplying enzymes (phaA$_{RE}$ and phaB$_{RE}$) from *Ralstonia eutropha* H16, and the PCR-cloned cp-pct gene was inserted into the SbfI/NdeI restriction site, thereby producing a pPs619C1300-CPPCT recombinant vector.

Similarly, various PHA synthase mutants were produced using the following primers. The produced mutants were arranged in the following Tables 2 through 5.

```
E130D
SEQ ID NO: 17: 5'-atc aac ctc atg acc gat gcg atg gcg ccg acc-3'
SEQ ID NO: 18: 5'-ggt cgg cgc cat cgc atc ggt cat gag gtt gat-3'
```

-continued

```
S325T
SEQ ID NO: 13: 5'-CTG ACC TTG CTG GTG ACC GTG CTT GAT ACC ACC-
3'
SEQ ID NO: 14: 5'-GGT GGT ATC AAG CAC GGT CAC CAG CAA GGT
CAG-3'

S477R
SEQ ID NO: 23: 5'-gaa ttc gtg ctg tcg agc cgc ggg cat atc-3'
SEQ ID NO: 24: 5'-gat atg ccc gcg gct cga cag cac gaa ttc-3'

S477H
SEQ ID NO: 25: 5'-gaa ttc gtg ctg tcg agc cat ggg cat atc-3'
SEQ ID NO: 26: 5'-gat atg ccc atg gct cga cag cac gaa ttc-3'

S477F
SEQ ID NO: 27: 5'-gaa ttc gtg ctg tcg agc ttt ggg cat atc-3'
SEQ ID NO: 28: 5'-gat atg ccc aaa gct cga cag cac gaa ttc-3'

S477Y
SEQ ID NO: 29: 5'-gaa ttc gtg ctg tcg agc tat ggg cat atc-3'
SEQ ID NO: 30: 5'-gat atg ccc ata gct cga cag cac gaa ttc-3'

S477G
SEQ ID NO: 31: 5'-gaa ttc gtg ctg tcg agc ggc ggg cat atc-3'
SEQ ID NO: 32: 5'-gat atg ccc gcc gct cga cag cac gaa ttc-3'

Q481K
SEQ ID NO: 33: 5'-ggg cat atc aaa agc atc ctg aac ccg c-3'
SEQ ID NO: 34: 5'-gcg ggt tca gga tgc ttt tga tat gcc c-3'

Q481M
SEQ ID NO: 35: 5'-ggg cat atc atg agc atc ctg aac ccg c-3'
SEQ ID NO: 36: 5'-gcg ggt tca gga tgc tca tga tat gcc c-3'

Q481R
SEQ ID NO: 37: 5'-ggg cat atc cgc agc atc ctg aac ccg c-3'
SEQ ID NO: 38: 5'-gcg ggt tca gga tgc tgc gga tat gcc c-3'
```

TABLE 2

| Recombinant synthase | Nucleic acid substitution | Amino acid substitution | Primer |
|---|---|---|---|
| pPs619C1200 | AGC → ACC<br>CAG → ATG | S325T<br>Q481M | SEQ ID NOs: 13 and 14<br>SEQ ID NOs: 35 and 36 |
| pPs619C1202 | GAA → GAT<br>CAG → AAA | E130D<br>Q481K | SEQ ID NOs: 17 and 18<br>SEQ ID NOs: 33 and 34 |
| pPs619C1203 | AGC → ACC<br>CAG → AAA | S325T<br>Q481K | SEQ ID NOs: 13 and 14<br>SEQ ID NOs: 33 and 34 |
| pPs619C1204 | GAA → GAT<br>CAG → ATG | E130D<br>Q481M | SEQ ID NOs: 17 and 18<br>SEQ ID NOs: 35 and 36 |
| pPs619C1205 | GAA → GAT<br>CAG → CGC | E130D<br>Q481R | SEQ ID NOs: 17 and 18<br>SEQ ID NOs: 37 and 38 |

TABLE 3

| Recombinant synthase | Nucleic acid substitution | Amino acid substitution | Primer |
|---|---|---|---|
| pPs619C1300 | GAA → GAT<br>AGC → ACC<br>CAG → ATG | E130D<br>S325T<br>Q481M | SEQ ID NOs: 17 and 18<br>SEQ ID NOs: 13 and 14<br>SEQ ID NOs: 35 and 36 |
| pPs619C1301 | GAA → GAT<br>AGC → ACC<br>CAG → AAA | E130D<br>S325T<br>Q481K | SEQ ID NOs: 17 and 18<br>SEQ ID NOs: 13 and 14<br>SEQ ID NOs: 33 and 34 |
| pPs619C1304 | GAA → GAT<br>AGC → CGC<br>CAG → AAA | E130D<br>S477R<br>Q481K | SEQ ID NOs: 17 and 18<br>SEQ ID NOs: 23 and 24<br>SEQ ID NOs: 33 and 34 |
| pPs619C1305 | GAA → GAT<br>AGC → CGC<br>CAG → ATG | E130D<br>S477R<br>Q481M | SEQ ID NOs: 17 and 18<br>SEQ ID NOs: 23 and 24<br>SEQ ID NOs: 35 and 36 |
| pPs619C1306 | GAA → GAT<br>AGC → CGC<br>CAG → CGC | E130D<br>S477R<br>Q481R | SEQ ID NOs: 17 and 18<br>SEQ ID NOs: 23 and 24<br>SEQ ID NOs: 37 and 38 |
| pPs619C1307 | GAA → GAT<br>AGC → CAT<br>CAG → AAA | E130D<br>S477H<br>Q481K | SEQ ID NOs: 17 and 18<br>SEQ ID NOs: 25 and 26<br>SEQ ID NOs: 33 and 34 |
| pPs619C1308 | GAA → GAT<br>AGC → CAT<br>CAG → ATG | E130D<br>S477H<br>Q481M | SEQ ID NOs: 17 and 18<br>SEQ ID NOs: 25 and 26<br>SEQ ID NOs: 35 and 36 |
| pPs619C1309 | GAA → GAT<br>AGC → CAT<br>CAG → CGC | E130D<br>S477H<br>Q481R | SEQ ID NOs: 17 and 18<br>SEQ ID NOs: 25 and 26<br>SEQ ID NOs: 37 and 38 |
| pPs619C1310 | GAA → GAT<br>AGC → TTT<br>CAG → AAA | E130D<br>S477F<br>Q481K | SEQ ID NOs: 17 and 18<br>SEQ ID NOs: 27 and 28<br>SEQ ID NOs: 33 and 34 |

TABLE 4

| Recombinant synthase | Nucleic acid substitution | Amino acid substitution | Primer |
|---|---|---|---|
| pPs619C1311 | GAA → GAT | E130D | SEQ ID NOs: 17 and 18 |
| | AGC → TTT | S477F | SEQ ID NOs: 27 and 28 |
| | CAG → ATG | Q481M | SEQ ID NOs: 35 and 36 |
| pPs619C1312 | GAA → GAT | E130D | SEQ ID NOs: 17 and 18 |
| | AGC → TTT | S477F | SEQ ID NOs: 27 and 28 |
| | CAG → CGC | Q481R | SEQ ID NOs: 37 and 38 |
| pPs619C1313 | GAA → GAT | E130D | SEQ ID NOs: 17 and 18 |
| | AGC → TAT | S477Y | SEQ ID NOs: 29 and 30 |
| | CAG → AAA | Q481K | SEQ ID NOs: 33 and 34 |
| pPs619C1314 | GAA → GAT | E130D | SEQ ID NOs: 17 and 18 |
| | AGC → TAT | S477Y | SEQ ID NOs: 29 and 30 |
| | CAG → ATG | Q481M | SEQ ID NOs: 35 and 36 |
| pPs619C1315 | GAA → GAT | E130D | SEQ ID NOs: 17 and 18 |
| | AGC → TAT | S477Y | SEQ ID NOs: 29 and 30 |
| | CAG → CGC | Q481R | SEQ ID NOs: 37 and 38 |

TABLE 5

| Recombinant synthase | Nucleic acid substitution | Amino acid substitution | Primer |
|---|---|---|---|
| pPs619C1400 | GAA → GAT | E130D | SEQ ID NOs: 17 and 18 |
| | AGC → ACC | S325T | SEQ ID NOs: 13 and 14 |
| | AGC → CGC | S477R | SEQ ID NOs: 23 and 24 |
| | CAG → ATG | Q481M | SEQ ID NOs: 35 and 36 |
| pPs619C1401 | GAA → GAT | E130D | SEQ ID NOs: 17 and 18 |
| | AGC → ACC | S325T | SEQ ID NOs: 13 and 14 |
| | AGC → CGC | S477R | SEQ ID NOs: 23 and 24 |
| | CAG → AAA | Q481K | SEQ ID NOs: 33 and 34 |
| pPs619C1334 | GAA → GAT | E130D | SEQ ID NOs: 17 and 18 |
| | AGC → ACC | S325T | SEQ ID NOs: 13 and 14 |
| | AGC → TTT | S477F | SEQ ID NOs: 27 and 28 |
| | CAG → ATG | Q481M | SEQ ID NOs: 35 and 36 |
| pPs619C1336 | GAA → GAT | E130D | SEQ ID NOs: 17 and 18 |
| | AGC → ACC | S325T | SEQ ID NOs: 13 and 14 |
| | AGC → GGC | S477G | SEQ ID NOs: 31 and 32 |
| | CAG → ATG | Q481M | SEQ ID NOs: 35 and 36 |
| pPs619C1339 | GAA → GAT | E130D | SEQ ID NOs: 17 and 18 |
| | AGC → ACC | S325T | SEQ ID NOs: 13 and 14 |
| | AGC → TTT | S477F | SEQ ID NOs: 27 and 28 |
| | CAG → AAA | Q481K | SEQ ID NOs: 33 and 34 |

Example 1-2

Preparation and Screening of a Library of a Mutant of Propionyl-COA Transferase from *Clostridium Propionicum*

As is known, when CP-PCT is overexpressed in *E. coli*, it causes serious metabolic disorder and exhibits toxicity. In general, all recombinant *E. coli* were dead at the same time with addition of an inducer in an isopropyl-β-D-thio-galactoside (IPTG)-inducible protein expression system using a tac promoter or T7 promoter, which is widely used to express recombinant proteins. For this reason, synthesis of PLA and PLA copolymer was succeeded using a constitutive expression system weakly but continuously expressing a gene with growth of a microorganism. In order to introduce random mutation on a cp-pct gene, pPs619C1300-CPPCT disclosed in Korean Patent Application No. 10-2006-0116234 was used as a template, $Mn^{2+}$ was added using primers of SEQ ID NOs: 39 and 40, and error-prone PCR was performed under conditions in which the concentrations of dNTPs varied.

SEQ ID NO: 39: 5'-cgc cgg cag gcc tgc agg-3'

SEQ ID NO: 40: 5'-ggc agg tca gcc cat atg tc-3'

Thereafter, in order to amplify a randomly mutated PCR fragment, PCR was performed under common conditions using the primer of SEQ ID NOs: 39 and 40. A pPs619C1300-CPPCT vector containing phaC1$_{Ps6-19}$300, which is a phaC1$_{Ps6-19}$ synthase, was cleaved with SbfI/NdeI to remove a wild-type cp-pct gene, and the amplified mutated PCR fragment was inserted into a SbfI/NdeI restriction site to produce a ligation mixture. The ligation mixture was introduced to *E. coli* JM109, thereby preparing a CP-PCT library with a scale of about ~$10^{-5}$. The prepared CP-PCT library was incubated for 3 days in a polymer detection medium (LB agar, glucose 20 g/L, 3HB 1 g/L, Nile red 0.5 μg/ml) and screened to confirm whether a polymer was produced, thereby primarily selecting up to 80 candidates. The candidates were grown for 4 days in a liquid medium (LB agar, glucose 20 g/L, 3HB 1 g/L, ampicillin 100 mg/L, 37° C.) under polymer-generating conditions and analyzed by florescence activated cell sorting (FACS), thereby selecting two final samples. In order to find out the positions of the prepared CP-PCT mutants, gene sequence analysis of the CP-PCT mutants was performed as shown in Table 6.

TABLE 6

| Recombinant vector | Nucleic acid substitution |
|---|---|
| CP-PCT Mutant 512 | A1200G |
| CP-PCT Mutant 522 | T78C, T669C, A1125G, T1158C |

Random mutagenesis was performed on the finally selected mutants 512 and 522 using the above-described error-prone PCR, thereby obtaining the following CP-PCT mutants 531-537.

TABLE 7

| | Mutations | Silent Mutations |
|---|---|---|
| CpPct512 | | A1200G |
| CpPct522 | | T78C, T669C, A1125G, T1158C |
| CpPct531 | Gly335Asp | A1200G |
| CpPct532 | Ala243Thr | A1200G |
| CpPct533 | Asp65Gly | T669C, A1125G, T1158C |
| CpPct534 | Asp257Asn | A1200G |
| CpPct535 | Asp65Asn | T669C, A1125G, T1158C |
| CpPct537 | Thr199Ile | T669C, A1125G, T1158C |
| CpPct540 | Val193Ala | T78C, T669C, A1125G, T1158C |

Thereafter, in order to amplify a PCR fragment including the CpPct532 mutant, a PCR method was performed under common conditions using the primers of SEQ ID NOs: 39 and 40. The pPs619C1300-CPPCT vector was cleaved with SbfI/NdeI to remove a wild-type CP-PCT gene, and the amplified CpPct532 PCR fragment was inserted into a SbfI/NdeI restriction site to produce a ligation mixture, thereby producing the pPs619C1300-CPPCT532 vector used in the following Example 1-3.

Example 1-3

Preparation of the pPs619C1300-CPPCT532 Vector

A PHA synthase mutant (phaC1$_{Ps6-19}$400) from *Pseudomonas* sp. 6-19, which has an amino-acid sequence in which E130D, S325T, S477R, and Q481M were mutated, was prepared using the phaC1$_{Ps6-19}$ synthase mutant (phaC1$_{Ps6-19}$300) by SDM using primers of SEQ ID NOs: 41 and 42.

```
SEQ ID NO: 41: 5'-ttc gtg ctg tcg agc aga ggg
cat atc-3'

SEQ ID NO: 42: 5'-gat atg ccc tct gct cga cag
cac gaa-3'
```

The resultant recombinant vector (pPs619C1400-CPPCT532) was transformed into *E. coli* JM109 and grown in a 3HB-containing polymer detection medium (LB agar, glucose 20 g/L, 3HB 2 g/L, Nile red 0.5 μg/ml). As a result, polymer production was detected.

Example 1-4

Preparation of a pPs619C1400CPPCT532ReAb Plasmid and Transformation of *E. Coli*

In order to produce plasmids containing phaC1$_{Ps6-19}$400, CPPCT532, phaA$_{RE}$, and phaB$_{RE}$ genes respectively encoding enzymes required for efficient production of PLA and PLA copolymer from sucrose, PCR cloning was performed with respect to a PHB-producting promoter pReC and phaA$_{RE}$ and phaB$_{RE}$ genes from *Ralstonia eutropha* H16 on a pSYL105 vector (Lee et al., Biotech. Bioeng., 1994, 44:1337-1347) using primers of SEQ ID NOs: 43 and 44 and primers of SEQ ID NOs: 45 and 46, respectively.

```
SEQ ID NO: 43: 5'-aga cat atg caa gta cct tgc cga
cat cta tg-3'

SEQ ID NO: 44: 5'-gat gac aac gtc agt cat gat ttg
att gtc tct ctg-3'

SEQ ID NO: 45: 5'-cag aga gac aat caa atc atg act
gac gtt gtc atc-3'

SEQ ID NO: 46: 5'-gca ggt cag ccc ata tgc ag-3'
```

A PCR reactant was purified on an agarose gel, and the overlapping PCR was performed using the PCR reactant as a template and the primers of SEQ ID NOs: 43 and 46. The PCR reactant and the pPs619C1400CPPCT532 vector were cleaved with NdeI, and the PCR reactant (pReC-phaABRE) was inserted into a NdeI restriction site of the pPs619C1400CPPCT532 vector, thereby completing a pPs619C1400CPPCT532ReAB vector as shown in FIG. 1. In the pPs619C1400CPPCT532ReAB vector, the PHB-producting promoter (pReC) was additionally inserted into the front portions of the phaA$_{RE}$ and phaB$_{RE}$ genes in order to further promote transcription of the target phaARE and phaBRE genes.

The recombinant vector (pPs619C1400CPPCT532ReAB) was transformed into *E. coli* JM109, and grown in a 3HB-free polymer detection medium (LB agar, glucose 20 g/L, Nile red 0.5 μg/ml). As a result, polymer production could be observed. Thus, it could be confirmed that the phaA$_{RE}$ and phaB$_{RE}$ genes additionally inserted into the pPs619C1400CPPCT532 vector were expressed and operated normally.

Example 2

Preparation of poly(3-hydroxybutyrate-co-lactate) (P(3HB-co-LA)) from a Recombinant *E. Coli* Using Sucrose as a Carbon Source A colony on an LB agar plate containing 100 mg/L of ampicillin as an antibiotic was inoculated into 3 mL of a LB medium containing 100 mg/L of ampicillin and cultured for 12 hours at 30° C., while being stirred at 200 rpm. 1 mL of the culture solution was inoculated into each of 100 mL methyl red (MR) medium and 100 mL LB medium, which contains 100 mg/L of ampicillin, 20 g/L of sucrose, and in some cases, 2 g/L of 3-hydroxybutyrate. Thereafter, each culture solution was cultured at about 30° C. for 4 days, while being stirred at 200 rpm. The initial pH of the MR medium was adjusted to pH 7 using 10 N NaOH. The medium samples used in the present culturing process are shown in the following Table 8.

After the culture was finished, biomasses were retrieved from the culture solutions. The retrieved cells were cleaned 3 times with distilled water and dried for 24 hours in a dryer maintained at about 100° C. The dried cells were partially collected and underwent gas chromatographic (GC) analysis, thereby measuring the content of P(3HB-co-LA) synthesized in cells. Standard materials used for the GC analysis were a P(3HB-co-3HV) copolymer (including about 12% by weight 3HV) and a PLA homopolymer. The GC analysis results are shown in the following Table 9. As can be seen from Table 9, biosynthesis of a P(3HB-co-LA) copolymer was enabled in both the MR and LB media irrespective of the addition of 3HB. Also, it could be confirmed that the biosynthesis of the P(3HB-co-LA) copolymer was more efficient in the MR medium than in the LB medium. Therefore, the P(3HB-co-LA) copolymer could be produced from sucrose using the recombinant *E. coli* according to the present invention.

TABLE 8

| Component | LB medium (/L) | MR medium (/L) |
|---|---|---|
| Trypsin | 10 g | — |
| Yeast extract | 5 g | — |
| NaCl | 10 g | — |
| KH$_2$PO$_4$ | — | 6.67 g |
| (NH$_4$)$_2$HPO$_4$ | — | 4 g |
| Citrate | — | 0.8 g |
| MgSO$_4$•H$_2$O | — | 0.8 g |
| 3HB | 0 g or 2 g | 0 g or 2 g |
| Sucrose | 20 g | 20 g |
| Tracer* | — | 5 mL |

*Tracer (/L): 10 g of FeSO$_4$•H$_2$O; 2.25 g of ZnSO$_4$•H$_2$O; 1 g of CuSO$_4$•H$_2$O; 0.5 g of MnSO$_4$•H$_2$O; 2 g of CaCl$_2$•H$_2$O; 0.23 g of Na$_2$B$_4$O$_7$•H$_2$O; 0.1 g of (NH$_4$)$_6$Mo$_7$O$_{24}$; 10 mL of 35% HCl.

TABLE 9

| Medium | Initial substrate | Type of biosynthesized polymer | Polymer content (weight ratio) | Content of LA in polymer (molar ratio) |
|---|---|---|---|---|
| MR | Su* | P(3HB-co-LA) | 13.41 | 12.03 |
| MR | Su, 3HB** | P(3HB-co-LA) | 21.74 | 9.15 |
| LB | Su | P(3HB-co-LA) | 2.68 | 17.49 |
| LB | Su, 3HB | P(3HB-co-LA) | 2.29 | 10.85 |

*Su: 20 g/L of sucrose
**3HB: 2 g/L of 3-hydroxybutyrate

While the invention has been shown and described with reference to certain examples thereof, it will be understood by those skilled in the art that various changes in form and details may be made therein without departing from the spirit and scope of the invention as defined by the appended claims.

The invention claimed is:

1. A method of producing a polylactate (PLA) or hydroxyalkanoate-lactate copolymer from sucrose, comprising:
    culturing or growing a microorganism in an environment containing lactate and sucrose or an environment containing lactate, sucrose, and hydroxyalkanoate, wherein the microorganism comprises a gene of an enzyme converting lactate into lactyl-CoA and a gene of a polyhydroxyalkanoate (PHA) synthase using lactyl-CoA as a substrate, and is capable of producing the PLA or hydroxyalkanoate-lactate copolymer using sucrose as a substrate, and wherein the gene of the PHA synthase using lactyl-CoA as the substrate has a base sequence corresponding to an amino-acid sequence in which at least one position selected from the group consisting of E130D, S325T, S477R, S477H, S477F, S477Y, S477G, Q481M, Q481K, and Q481R is mutated in SEQ ID NO: 4; and
    harvesting the PLA or hydroxyalkanoate-lactate copolymer from the microorganism.

2. The method according to claim 1, wherein the microorganism is obtained by transforming a microorganism that does not include at least one of the gene of the enzyme converting lactate into lactyl-CoA and the gene of the PHA synthase using lactyl-CoA as the substrate and is capable of using sucrose as a substrate, with at least one of the gene of the enzyme converting lactate into lactyl-CoA and the gene of the PHA synthase using lactyl-CoA as the substrate.

3. The method according to claim 1, wherein hydroxyalkanoate of the hydroxyalkanoate-lactate copolymer is at least one selected from the group consisting of 3-hydroxybutyrate, 3-hydroxyvalerate, 4-hydroxybutyrate, medium chain-length (D)-3-hydroxycarboxylic acid with 6 to 14 carbon atoms, 2-hydroxypropionic acid, 3-hydroxypropionic acid, 3-hydroxyhexanoic acid, 3-hydroxyheptanoic acid, 3-hydroxyoctanoic acid, 3-hydroxynonanoic acid, 3-hydroxydecanoic acid, 3-hydroxyundecanoic acid, 3-hydroxydodecanoic acid, 3-hydroxytetradecanoic acid, 3-hydroxyhexadecanoic acid, 4-hydroxyvaleric acid, 4-hydroxyhexanoic acid, 4-hydroxyheptanoic acid, 4-hydroxyoctanoic acid, 4-hydroxydecanoic acid, 5-hydroxyvaleric acid, 5-hydroxyhexanoic acid, 6-hydroxydodecanoic acid, 3-hydroxy-4-pentenoic acid, 3-hydroxy-4-trans-hexenoic acid, 3-hydroxy-4-cis-hexenoic acid, 3-hydroxy-5-hexenoic acid, 3-hydroxy-6-trans-octenoic acid, 3-hydroxy-6-cis-octenoic acid, 3-hydroxy-7-octenoic acid, 3-hydroxy-8-nonenoic acid, 3-hydroxy-9-decenoic acid, 3-hydroxy-5-cis-dodecenoic acid, 3-hydroxy-6-cis-dodecenoic acid, 3-hydroxy-5-cis-tetradecenoic acid, 3-hydroxy-7-cis-tetradecenoic acid, 3-hydroxy-5,8-cis-cis-tetradecenoic acid, 3-hydroxy-4-methylvaleric acid, 3-hydroxy-4-methylhexanoic acid, 3-hydroxy-5-methylhexanoic acid, 3-hydroxy-6-methylheptanoic acid, 3-hydroxy-4-methyloctanoic acid, 3-hydroxy-5-methyloctanoic acid, 3-hydroxy-6-methyloctanoic acid, 3-hydroxy-7-methyloctanoic acid, 3-hydroxy-6-methylnonanoic acid, 3-hydroxy-7-methylnonanoic acid, 3-hydroxy-8-methylnonanoic acid, 3-hydroxy-7-methyldecanoic acid, 3-hydroxy-9-methyldecanoic acid, 3-hydroxy-7-methyl-6-octenoic acid, malic acid, 3-hydroxysuccinic acid-methylester, 3-hydroxyadipinic acid-methylester, 3-hydroxysuberic acid-methylester, 3-hydroxyazelaic acid-methylester, 3-hydroxysebacic acid-methylester, 3-hydroxysuberic acid-ethylester, 3-hydroxysebacic acid-ethylester, 3-hydroxypimelic acid-propylester, 3-hydroxysebacic acid-benzylester, 3-hydroxy-8-acetoxyoctanoic acid, 3-hydroxy-9-acetoxynonanoic acid, phenoxy-3-hydroxybutyric acid, phenoxy-3-hydroxyvaleric acid, phenoxy-3-hydroxyheptanoic acid, phenoxy-3-hydroxyoctanoic acid, para-cyanophenoxy-3-hydroxybutyric acid, para-cyanophenoxy-3-hydroxyvaleric acid, para-cyanophenoxy-3-hydroxyhexanoic acid, para-nitrophenoxy-3-hydroxyhexanoic acid, 3-hydroxy-5-phenylvaleric acid, 3-hydroxy-5-cyclohexylbutyric acid, 3,12-dihydroxydodecanoic acid, 3,8-dihydroxy-5-cis-tetradecenoic acid, 3-hydroxy-4,5-epoxydecanoic acid, 3-hydroxy-6,7-epoxydodecanoic acid, 3-hydroxy-8,9-epoxy-5,6-cis-tetradecenoic acid, 7-cyano-3-hydroxyheptanoic acid, 9-cyano-3-hydroxynonanoic acid, 3-hydroxy-7-fluoroheptanoic acid, 3-hydroxy-9-fluorononanoic acid, 3-hydroxy-6-chlorohexanoic acid, 3-hydroxy-8-chlorooctanoic acid, 3-hydroxy-6-bromohexanoic acid, 3-hydroxy-8-bromooctanoic acid, 3-hydroxy-11-bromoundecanoic acid, 3-hydroxy-2-butenoic acid, 6-hydroxy-3-dodecenoic acid, 3-hydroxy-2-methylbutyric acid, 3-hydroxy-2-methylvaleric acid, and 3-hydroxy-2,6-dimethyl-5-heptenoic acid.

4. The method according to claim 1, wherein the gene of the enzyme converting lactate into lactyl-CoA is a propionyl-CoA transferase gene (pct).

5. The method according to claim 1, wherein the gene of the enzyme converting lactate into lactyl-CoA is a pct gene from *Clostridium propionicum*.

6. The method according to claim 1, wherein the gene of the enzyme converting lactate into lactyl-CoA has
a base sequence obtained by mutating T78C, T669C, A1125G, and T1158C in the base sequence of SEQ ID NO: 1 and mutating Val193Ala in the amino-acid sequence of SEQ ID NO: 2.

7. The method according to claim 1, wherein the gene of the enzyme converting lactate into lactyl-CoA has a base sequence obtained by mutating A1200G in the base sequence of SEQ ID NO: 1 and mutating Ala243Thr in the amino-acid sequence of SEQ ID NO: 2.

8. The method according to claim 1, wherein the gene of the PHA synthase using lactyl-CoA as the substrate is a gene of a PHA synthase from *pseudomonas* sp. 6-19.

9. The method according to claim 1, wherein the gene of the PHA synthase using lactyl-CoA as the substrate has a base sequence corresponding to an amino-acid sequence in which E130D, S325T, S477R, and Q481M are mutated in SEQ ID NO: 4.

10. The method according to claim 1, wherein the microorganism further comprises a gene of an enzyme producing hydroxyacyl-CoA from sucrose.

11. The method according to claim 10, wherein the enzyme producing hydroxyacyl-CoA from sucrose is a ketothiolase and an acetoacetyl-CoA reductase.

12. The method according to claim 11, wherein the ketothiolase and the acetoacetyl-CoA reductase are derived from *Ralstonia eutropha*.

13. The method according to claim 1, wherein the microorganism is a bacterium.

14. The method according to claim 13, wherein the bacterium is an *E. coli*.

\* \* \* \* \*

SEQUENCE LISTING

<160> NUMBER OF SEQ ID NOS: 47

<210> SEQ ID NO 1
<211> LENGTH: 1572
<212> TYPE: DNA
<213> ORGANISM: Clostridium propionicum
<220> FEATURE:
<223> OTHER INFORMATION: propionyl-CoA transferase

<400> SEQUENCE: 1

| | | | | | | |
|---|---|---|---|---|---|---|
| atgagaaagg | ttcccattat | taccgcagat | gaggctgcaa | agcttattaa | agacggtgat | 60 |
| acagttacaa | caagtggttt | cgttggaaat | gcaatccctg | aggctcttga | tagagctgta | 120 |
| gaaaaaagat | tcttagaaac | aggcgaaccc | aaaaacatta | cctatgttta | ttgtggttct | 180 |
| caaggtaaca | gagacggaag | aggtgctgag | cactttgctc | atgaaggcct | tttaaaacgt | 240 |
| tacatcgctg | gtcactgggc | tacagttcct | gctttgggta | aaatggctat | ggaaaataaa | 300 |
| atggaagcat | ataatgtatc | tcagggtgca | ttgtgtcatt | tgttccgtga | tatagcttct | 360 |
| cataagccag | gcgtatttac | aaaggtaggt | atcggtactt | tcattgaccc | cagaaatggc | 420 |
| ggcggtaaag | taaatgatat | taccaaagaa | gatattgttg | aattggtaga | gattaagggt | 480 |
| caggaatatt | tattctaccc | tgcttttcct | attcatgtag | ctcttattcg | tggtacttac | 540 |
| gctgatgaaa | gcggaaatat | cacatttgag | aaagaagttg | ctcctctgga | aggaacttca | 600 |
| gtatgccagg | ctgttaaaaa | cagtggcggt | atcgttgtag | ttcaggttga | aagagtagta | 660 |
| aaagctggta | ctcttgaccc | tcgtcatgta | aaagttccag | gaatttatgt | tgactatgtt | 720 |
| gttgttgctg | acccagaaga | tcatcagcaa | tctttagatt | gtgaatatga | tcctgcatta | 780 |
| tcaggcgagc | atagaagacc | tgaagttgtt | ggagaaccac | ttcctttgag | tgcaaagaaa | 840 |
| gttattggtc | gtcgtggtgc | cattgaatta | gaaaaagatg | ttgctgtaaa | tttaggtgtt | 900 |
| ggtgcgcctg | aatatgtagc | aagtgttgct | gatgaagaag | gtatcgttga | tttttatgact | 960 |
| ttaactgctg | aaagtggtgc | tattggtggt | gttcctgctg | gtggcgttcg | ctttggtgct | 1020 |
| tcttataatg | cggatgcatt | gatcgatcaa | ggttatcaat | tcgattacta | tgatggcggc | 1080 |
| ggcttagacc | tttgctattt | aggcttagct | gaatgcgatg | aaaaaggcaa | tatcaacgtt | 1140 |
| tcaagatttg | gccctcgtat | cgctggttgt | ggtggtttca | tcaacattac | acagaataca | 1200 |
| cctaaggtat | tcttctgtgg | tactttcaca | gcaggtggct | taaaggttaa | aattgaagat | 1260 |
| ggcaaggtta | ttattgttca | agaaggcaag | cagaaaaaat | tcttgaaagc | tgttgagcag | 1320 |
| attacattca | atggtgacgt | tgcacttgct | aataagcaac | aagtaactta | tattacagaa | 1380 |
| agatgcgtat | tcctttttgaa | ggaagatggt | ttgcacttat | ctgaaattgc | acctggtatt | 1440 |
| gatttgcaga | cacagattct | tgacgttatg | gattttgcac | ctattattga | cagagatgca | 1500 |
| aacggccaaa | tcaaattgat | ggacgctgct | ttgtttgcag | aaggcttaat | gggtctgaag | 1560 |
| gaaatgaagt | cc | | | | | 1572 |

<210> SEQ ID NO 2
<211> LENGTH: 524
<212> TYPE: PRT
<213> ORGANISM: Clostridium propionicum
<220> FEATURE:
<223> OTHER INFORMATION: propionyl-CoA transferase

```
<400> SEQUENCE: 2

Met Arg Lys Val Pro Ile Ile Thr Ala Asp Glu Ala Ala Lys Leu Ile
 1               5                  10                  15

Lys Asp Gly Asp Thr Val Thr Thr Ser Gly Phe Val Gly Asn Ala Ile
             20                  25                  30

Pro Glu Ala Leu Asp Arg Ala Val Glu Lys Arg Phe Leu Glu Thr Gly
         35                  40                  45

Glu Pro Lys Asn Ile Thr Tyr Val Tyr Cys Gly Ser Gln Gly Asn Arg
     50                  55                  60

Asp Gly Arg Gly Ala Glu His Phe Ala His Gly Leu Leu Lys Arg
 65                  70                  75                  80

Tyr Ile Ala Gly His Trp Ala Thr Val Pro Ala Leu Gly Lys Met Ala
                 85                  90                  95

Met Glu Asn Lys Met Glu Ala Tyr Asn Val Ser Gln Gly Ala Leu Cys
            100                 105                 110

His Leu Phe Arg Asp Ile Ala Ser His Lys Pro Gly Val Phe Thr Lys
        115                 120                 125

Val Gly Ile Gly Thr Phe Ile Asp Pro Arg Asn Gly Gly Lys Val
130                 135                 140

Asn Asp Ile Thr Lys Glu Asp Ile Val Glu Leu Val Glu Ile Lys Gly
145                 150                 155                 160

Gln Glu Tyr Leu Phe Tyr Pro Ala Phe Pro Ile His Val Ala Leu Ile
                165                 170                 175

Arg Gly Thr Tyr Ala Asp Glu Ser Gly Asn Ile Thr Phe Glu Lys Glu
            180                 185                 190

Val Ala Pro Leu Glu Gly Thr Ser Val Cys Gln Ala Val Lys Asn Ser
        195                 200                 205

Gly Gly Ile Val Val Gln Val Glu Arg Val Val Lys Ala Gly Thr
210                 215                 220

Leu Asp Pro Arg His Val Lys Val Pro Gly Ile Tyr Val Asp Tyr Val
225                 230                 235                 240

Val Val Ala Asp Pro Glu Asp His Gln Gln Ser Leu Asp Cys Glu Tyr
                245                 250                 255

Asp Pro Ala Leu Ser Gly Glu His Arg Arg Pro Glu Val Val Gly Glu
            260                 265                 270

Pro Leu Pro Leu Ser Ala Lys Lys Val Ile Gly Arg Gly Ala Ile
        275                 280                 285

Glu Leu Glu Lys Asp Val Ala Val Asn Leu Gly Val Gly Ala Pro Glu
    290                 295                 300

Tyr Val Ala Ser Val Ala Asp Glu Glu Gly Ile Val Asp Phe Met Thr
305                 310                 315                 320

Leu Thr Ala Glu Ser Gly Ala Ile Gly Gly Val Pro Ala Gly Gly Val
                325                 330                 335

Arg Phe Gly Ala Ser Tyr Asn Ala Asp Ala Leu Ile Asp Gln Gly Tyr
            340                 345                 350

Gln Phe Asp Tyr Tyr Asp Gly Gly Gly Leu Asp Leu Cys Tyr Leu Gly
        355                 360                 365

Leu Ala Glu Cys Asp Glu Lys Gly Asn Ile Asn Val Ser Arg Phe Gly
370                 375                 380

Pro Arg Ile Ala Gly Cys Gly Gly Phe Ile Asn Ile Thr Gln Asn Thr
385                 390                 395                 400

Pro Lys Val Phe Phe Cys Gly Thr Phe Thr Ala Gly Gly Leu Lys Val
                405                 410                 415
```

```
Lys Ile Glu Asp Gly Lys Val Ile Val Gln Glu Gly Lys Gln Lys
            420                 425                 430

Lys Phe Leu Lys Ala Val Glu Gln Ile Thr Phe Asn Gly Asp Val Ala
            435                 440                 445

Leu Ala Asn Lys Gln Gln Val Thr Tyr Ile Thr Glu Arg Cys Val Phe
450                 455                 460

Leu Leu Lys Glu Asp Gly Leu His Leu Ser Glu Ile Ala Pro Gly Ile
465                 470                 475                 480

Asp Leu Gln Thr Gln Ile Leu Asp Val Met Asp Phe Ala Pro Ile Ile
                485                 490                 495

Asp Arg Asp Ala Asn Gly Gln Ile Lys Leu Met Asp Ala Ala Leu Phe
                500                 505                 510

Ala Glu Gly Leu Met Gly Leu Lys Glu Met Lys Ser
            515                 520

<210> SEQ ID NO 3
<211> LENGTH: 1677
<212> TYPE: DNA
<213> ORGANISM: Unknown
<220> FEATURE:
<223> OTHER INFORMATION: PHA synthase

<400> SEQUENCE: 3
atgagtaaca agagtaacga tgagttgaag tatcaagcct ctgaaaacac cttggggctt      60
aatcctgtcg ttgggctgcg tggaaaggat ctactggctt ctgctcgaat ggtgcttagg     120
caggccatca agcaaccggt gcacagcgtc aaacatgtcg cgcactttgg tcttgaactc     180
aagaacgtac tgctgggtaa atccgggctg caaccgacca gcgatgaccg tcgcttcgcc     240
gatccggcct ggagccagaa cccgctctat aaacgttatt tgcaaaccta cctggcgtgg     300
cgcaaggaac tccacgactg gatcgatgaa agtaacctcg ccccaagga tgtggcgcgt     360 gggcacttcg tgatcaacct catgaccgaa gcgatggcgc cgaccaacac cgcggccaac     420
ccggcggcag tcaaacgctt ttttgaaacc ggtggcaaaa gcctgctcga cggcctctcg     480
cacctggcca aggatctggt acacaacggc ggcatgccga gccaggtcaa catgggtgca     540
ttcgaggtcg gcaagagcct gggcgtgacc gaaggcgcgg tggtgtttcg caacgatgtg     600
ctggaactga tccagtacaa gccgaccacc gagcaggtat acgaacgccc gctgctggtg     660
gtgccgccgc agatcaacaa gttctacgtt ttcgacctga gcccggacaa gagcctggcg     720
cggttctgcc tgcgcaacaa cgtgcaaacg ttcatcgtca gctggcgaaa tcccaccaag     780
gaacagcgag agtggggcct gtcgacctac atcgaagccc tcaaggaagc ggttgacgtc     840
gttaccgcga tcaccggcag caaagacgtg aacatgctcg gggcctgctc cggcggcatc     900
acttgcactg cgctgctggg ccattacgcg gcgattggcg aaaacaaggt caacgccctg     960
accttgctgg tgagcgtgct tgataccacc tcgacagcg acgtcgccct gttcgtcaat    1020 gaacagacccc ttgaagccgc caagcgccac tcgtaccagg ccggcgtact ggaaggccgc    1080
gacatggcga aggtcttcgc ctggatgcgc cccaacgatc tgatcctgga ctactgggtc    1140
aacaattacc tgctaggcaa cgaaccgccg gtgttcgaca tcctgttctg gaacaacgac    1200
accacacggt tgcccgcggc gttccacgga gaccctgatcg aactgttcaa aaataaccca    1260
ctgattcgcc cgaatgcact ggaagtgtgc ggcacccca tcgacctcaa gcaggtgacg    1320
gccgacatct ttccctggc cggcaccaac gaccacatca cccccgtggaa gtcctgctac    1380 aagtcggcgc aactgtttgg cggcaacgtt gaattcgtgc tgtcgagcag cgggcatatc    1440
```

```
cagagcatcc tgaacccgcc gggcaatccg aaatcgcgct acatgaccag caccgaagtg    1500
gcggaaaatg ccgatgaatg caagcgaat gccaccaagc atacagattc ctggtggctg     1560
cactggcagg cctggcaggc ccaacgctcg ggcgagctga aaagtcccc gacaaaactg     1620 ggcagcaagg cgtatccggc aggtgaagcg gcgccaggca cgtacgtgca cgaacgg      1677
```

<210> SEQ ID NO 4
<211> LENGTH: 559
<212> TYPE: PRT
<213> ORGANISM: Unknown
<220> FEATURE:
<223> OTHER INFORMATION: PHA synthase

<400> SEQUENCE: 4

```
Met Ser Asn Lys Ser Asn Asp Glu Leu Lys Tyr Gln Ala Ser Glu Asn
 1               5                  10                  15

Thr Leu Gly Leu Asn Pro Val Val Gly Leu Arg Gly Lys Asp Leu Leu
            20                  25                  30

Ala Ser Ala Arg Met Val Leu Arg Gln Ala Ile Lys Gln Pro Val His
        35                  40                  45

Ser Val Lys His Val Ala His Phe Gly Leu Glu Leu Lys Asn Val Leu
    50                  55                  60

Leu Gly Lys Ser Gly Leu Gln Pro Thr Ser Asp Asp Arg Arg Phe Ala
65                  70                  75                  80

Asp Pro Ala Trp Ser Gln Asn Pro Leu Tyr Lys Arg Tyr Leu Gln Thr
                85                  90                  95

Tyr Leu Ala Trp Arg Lys Glu Leu His Asp Trp Ile Asp Glu Ser Asn
            100                 105                 110

Leu Ala Pro Lys Asp Val Ala Arg Gly His Phe Val Ile Asn Leu Met
        115                 120                 125

Thr Glu Ala Met Ala Pro Thr Asn Thr Ala Ala Asn Pro Ala Ala Val
    130                 135                 140

Lys Arg Phe Phe Glu Thr Gly Gly Lys Ser Leu Leu Asp Gly Leu Ser
145                 150                 155                 160

His Leu Ala Lys Asp Leu Val His Asn Gly Gly Met Pro Ser Gln Val
                165                 170                 175

Asn Met Gly Ala Phe Glu Val Gly Lys Ser Leu Gly Val Thr Glu Gly
            180                 185                 190

Ala Val Val Phe Arg Asn Asp Val Leu Glu Leu Ile Gln Tyr Lys Pro
        195                 200                 205

Thr Thr Glu Gln Val Tyr Glu Arg Pro Leu Leu Val Val Pro Pro Gln
    210                 215                 220

Ile Asn Lys Phe Tyr Val Phe Asp Leu Ser Pro Asp Lys Ser Leu Ala
225                 230                 235                 240

Arg Phe Cys Leu Arg Asn Asn Val Gln Thr Phe Ile Val Ser Trp Arg
                245                 250                 255

Asn Pro Thr Lys Glu Gln Arg Glu Trp Gly Leu Ser Thr Tyr Ile Glu
            260                 265                 270

Ala Leu Lys Glu Ala Val Asp Val Val Thr Ala Ile Thr Gly Ser Lys
        275                 280                 285

Asp Val Asn Met Leu Gly Ala Cys Ser Gly Gly Ile Thr Cys Thr Ala
    290                 295                 300

Leu Leu Gly His Tyr Ala Ala Ile Gly Glu Asn Lys Val Asn Ala Leu
305                 310                 315                 320

Thr Leu Leu Val Ser Val Leu Asp Thr Thr Leu Asp Ser Asp Val Ala
                325                 330                 335
```

```
Leu Phe Val Asn Glu Gln Thr Leu Glu Ala Ala Lys Arg His Ser Tyr
            340                 345                 350

Gln Ala Gly Val Leu Glu Gly Arg Asp Met Ala Lys Val Phe Ala Trp
        355                 360                 365

Met Arg Pro Asn Asp Leu Ile Trp Asn Tyr Trp Val Asn Asn Tyr Leu
    370                 375                 380

Leu Gly Asn Glu Pro Pro Val Phe Asp Ile Leu Phe Trp Asn Asn Asp
385                 390                 395                 400

Thr Thr Arg Leu Pro Ala Ala Phe His Gly Asp Leu Ile Glu Leu Phe
                405                 410                 415

Lys Asn Asn Pro Leu Ile Arg Pro Asn Ala Leu Glu Val Cys Gly Thr
                420                 425                 430

Pro Ile Asp Leu Lys Gln Val Thr Ala Asp Ile Phe Ser Leu Ala Gly
                435                 440                 445

Thr Asn Asp His Ile Thr Pro Trp Lys Ser Cys Tyr Lys Ser Ala Gln
            450                 455                 460

Leu Phe Gly Gly Asn Val Glu Phe Val Leu Ser Ser Gly His Ile
465                 470                 475                 480

Gln Ser Ile Leu Asn Pro Pro Gly Asn Pro Lys Ser Arg Tyr Met Thr
                485                 490                 495

Ser Thr Glu Val Ala Glu Asn Ala Asp Glu Trp Gln Ala Asn Ala Thr
            500                 505                 510

Lys His Thr Asp Ser Trp Trp Leu His Trp Gln Ala Trp Gln Ala Gln
            515                 520                 525

Arg Ser Gly Glu Leu Lys Lys Ser Pro Thr Leu Leu Gly Ser Lys Ala
        530                 535                 540

Tyr Pro Ala Gly Glu Ala Ala Pro Gly Thr Tyr Val His Glu Arg
545                 550                 555

<210> SEQ ID NO 5
<211> LENGTH: 35
<212> TYPE: DNA
<213> ORGANISM: Artificial Sequence
<220> FEATURE:
<223> OTHER INFORMATION: Primer

<400> SEQUENCE: 5
gagagacaat caaatcatga gtaacaagag taacg                          35

<210> SEQ ID NO 6
<211> LENGTH: 33
<212> TYPE: DNA
<213> ORGANISM: Artificial Sequence
<220> FEATURE:
<223> OTHER INFORMATION: Primer

<400> SEQUENCE: 6
cactcatgca agcgtcaccg ttcgtgcacg tac                            33

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
atgcccggag ccggttcgaa                                           20
```

<210> SEQ ID NO 8
<211> LENGTH: 35
<212> TYPE: DNA
<213> ORGANISM: Artificial Sequence
<220> FEATURE:
<223> OTHER INFORMATION: Primer

<400> SEQUENCE: 8
cgttactctt gttactcatg atttgattgt ctctc                          35

<210> SEQ ID NO 9
<211> LENGTH: 35
<212> TYPE: DNA
<213> ORGANISM: Artificial Sequence
<220> FEATURE:
<223> OTHER INFORMATION: Primer

<400> SEQUENCE: 9
gagagacaat caaatcatga gtaacaagag taacg                          35

<210> SEQ ID NO 10
<211> LENGTH: 33
<212> TYPE: DNA
<213> ORGANISM: Artificial Sequence
<220> FEATURE:
<223> OTHER INFORMATION: Primer

<400> SEQUENCE: 10
cactcatgca agcgtcaccg ttcgtgcacg tac                            33

<210> SEQ ID NO 11
<211> LENGTH: 33
<212> TYPE: DNA
<213> ORGANISM: Artificial Sequence
<220> FEATURE:
<223> OTHER INFORMATION: Primer

<400> SEQUENCE: 11
gtacgtgcac gaacggtgac gcttgcatga gtg                            33

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
aacgggaggg aacctgcagg                                           20

<210> SEQ ID NO 13
<211> LENGTH: 33
<212> TYPE: DNA
<213> ORGANISM: Artificial Sequence
<220> FEATURE:
<223> OTHER INFORMATION: Primer

<400> SEQUENCE: 13
ctgaccttgc tggtgaccgt gcttgatacc acc                            33

<210> SEQ ID NO 14
<211> LENGTH: 33
<212> TYPE: DNA
<213> ORGANISM: Artificial Sequence
<220> FEATURE:
<223> OTHER INFORMATION: Primer

<400> SEQUENCE: 14
ggtggtatca agcacggtca ccagcaaggt cag         33

<210> SEQ ID NO 15
<211> LENGTH: 36
<212> TYPE: DNA
<213> ORGANISM: Artificial Sequence
<220> FEATURE:
<223> OTHER INFORMATION: Primer

<400> SEQUENCE: 15
cgagcagcgg gcatatcatg agcatcctga acccgc      36

<210> SEQ ID NO 16
<211> LENGTH: 36
<212> TYPE: DNA
<213> ORGANISM: Artificial Sequence
<220> FEATURE:
<223> OTHER INFORMATION: Primer

<400> SEQUENCE: 16
gcgggttcag gatgctcatg atatgcccgc tgctcg      36

<210> SEQ ID NO 17
<211> LENGTH: 33
<212> TYPE: DNA
<213> ORGANISM: Artificial Sequence
<220> FEATURE:
<223> OTHER INFORMATION: Primer

<400> SEQUENCE: 17
atcaacctca tgaccgatgc gatggcgccg acc         33

<210> SEQ ID NO 18
<211> LENGTH: 33
<212> TYPE: DNA
<213> ORGANISM: Artificial Sequence
<220> FEATURE:
<223> OTHER INFORMATION: Primer

<400> SEQUENCE: 18
ggtcggcgcc atcgcatcgg tcatgaggtt gat         33

<210> SEQ ID NO 19
<211> LENGTH: 39
<212> TYPE: DNA
<213> ORGANISM: Artificial Sequence
<220> FEATURE:
<223> OTHER INFORMATION: Primer

<400> SEQUENCE: 19
ggaattcatg agaaaggttc ccattattac cgcagatga   39

<210> SEQ ID NO 20
<211> LENGTH: 46
<212> TYPE: DNA
<213> ORGANISM: Artificial Sequence
<220> FEATURE:
<223> OTHER INFORMATION: Primer

<400> SEQUENCE: 20
gctctagatt aggacttcat ttccttcaga cccattaagc cttctg   46

<210> SEQ ID NO 21
<211> LENGTH: 32
<212> TYPE: DNA
<213> ORGANISM: Artificial Sequence

```
<220> FEATURE:
<223> OTHER INFORMATION: Primer

<400> SEQUENCE: 21
aggcctgcag gcggataaca atttcacaca gg                                   32

<210> SEQ ID NO 22
<211> LENGTH: 31
<212> TYPE: DNA
<213> ORGANISM: Artificial Sequence
<220> FEATURE:
<223> OTHER INFORMATION: Primer

<400> SEQUENCE: 22
gcccatatgt ctagattagg acttcatttc c                                    31

<210> SEQ ID NO 23
<211> LENGTH: 30
<212> TYPE: DNA
<213> ORGANISM: Artificial Sequence
<220> FEATURE:
<223> OTHER INFORMATION: primer

<400> SEQUENCE: 23
gaattcgtgc tgtcgagccg cgggcatatc                                      30

<210> SEQ ID NO 24
<211> LENGTH: 30
<212> TYPE: DNA
<213> ORGANISM: Artificial Sequence
<220> FEATURE:
<223> OTHER INFORMATION: primer

<400> SEQUENCE: 24
gatatgcccg cggctcgaca gcacgaattc                                      30

<210> SEQ ID NO 25
<211> LENGTH: 30
<212> TYPE: DNA
<213> ORGANISM: Artificial Sequence
<220> FEATURE:
<223> OTHER INFORMATION: primer

<400> SEQUENCE: 25
gaattcgtgc tgtcgagcca tgggcatatc                                      30

<210> SEQ ID NO 26
<211> LENGTH: 30
<212> TYPE: DNA
<213> ORGANISM: Artificial Sequence
<220> FEATURE:
<223> OTHER INFORMATION: primer

<400> SEQUENCE: 26
gatatgccca tggctcgaca gcacgaattc                                      30

<210> SEQ ID NO 27
<211> LENGTH: 30
<212> TYPE: DNA
<213> ORGANISM: Artificial Sequence
<220> FEATURE:
<223> OTHER INFORMATION: primer

<400> SEQUENCE: 27
gaattcgtgc tgtcgagctt tgggcatatc                                      30
```

```
<210> SEQ ID NO 28
<211> LENGTH: 30
<212> TYPE: DNA
<213> ORGANISM: Artificial Sequence
<220> FEATURE:
<223> OTHER INFORMATION: primer

<400> SEQUENCE: 28
gatatgccca aagctcgaca gcacgaattc                                    30

<210> SEQ ID NO 29
<211> LENGTH: 30
<212> TYPE: DNA
<213> ORGANISM: Artificial Sequence
<220> FEATURE:
<223> OTHER INFORMATION: primer

<400> SEQUENCE: 29
gaattcgtgc tgtcgagcta tgggcatatc                                    30

<210> SEQ ID NO 30
<211> LENGTH: 30
<212> TYPE: DNA
<213> ORGANISM: Artificial Sequence
<220> FEATURE:
<223> OTHER INFORMATION: primer

<400> SEQUENCE: 30
gatatgccca tagctcgaca gcacgaattc                                    30

<210> SEQ ID NO 31
<211> LENGTH: 30
<212> TYPE: DNA
<213> ORGANISM: Artificial Sequence
<220> FEATURE:
<223> OTHER INFORMATION: primer

<400> SEQUENCE: 31
gaattcgtgc tgtcgagcgg cgggcatatc                                    30

<210> SEQ ID NO 32
<211> LENGTH: 30
<212> TYPE: DNA
<213> ORGANISM: Artificial Sequence
<220> FEATURE:
<223> OTHER INFORMATION: primer

<400> SEQUENCE: 32
gatatgcccg ccgctcgaca gcacgaattc                                    30

<210> SEQ ID NO 33
<211> LENGTH: 28
<212> TYPE: DNA
<213> ORGANISM: Artificial Sequence
<220> FEATURE:
<223> OTHER INFORMATION: primer

<400> SEQUENCE: 33
gggcatatca aaagcatcct gaacccgc                                      28

<210> SEQ ID NO 34
<211> LENGTH: 28
<212> TYPE: DNA
<213> ORGANISM: Artificial Sequence
<220> FEATURE:
<223> OTHER INFORMATION: primer

<400> SEQUENCE: 34
```
gcgggttcag gatgcttttg atatgccc             28

<210> SEQ ID NO 35
<211> LENGTH: 28
<212> TYPE: DNA
<213> ORGANISM: Artificial Sequence
<220> FEATURE:
<223> OTHER INFORMATION: primer

<400> SEQUENCE: 35
gggcatatca tgagcatcct gaacccgc             28

<210> SEQ ID NO 36
<211> LENGTH: 28
<212> TYPE: DNA
<213> ORGANISM: Artificial Sequence
<220> FEATURE:
<223> OTHER INFORMATION: primer

<400> SEQUENCE: 36
gcgggttcag gatgctcatg atatgccc             28

<210> SEQ ID NO 37
<211> LENGTH: 28
<212> TYPE: DNA
<213> ORGANISM: Artificial Sequence
<220> FEATURE:
<223> OTHER INFORMATION: primer

<400> SEQUENCE: 37
gggcatatcc gcagcatcct gaacccgc             28

<210> SEQ ID NO 38
<211> LENGTH: 28
<212> TYPE: DNA
<213> ORGANISM: Artificial Sequence
<220> FEATURE:
<223> OTHER INFORMATION: primer

<400> SEQUENCE: 38
gcgggttcag gatgctgcgg atatgccc             28

<210> SEQ ID NO 39
<211> LENGTH: 18
<212> TYPE: DNA
<213> ORGANISM: Artificial Sequence
<220> FEATURE:
<223> OTHER INFORMATION: primer

<400> SEQUENCE: 39
cgccggcagg cctgcagg                        18

<210> SEQ ID NO 40
<211> LENGTH: 20
<212> TYPE: DNA
<213> ORGANISM: Artificial Sequence
<220> FEATURE:
<223> OTHER INFORMATION: primer

<400> SEQUENCE: 40
ggcaggtcag cccatatgtc                      20

<210> SEQ ID NO 41
<211> LENGTH: 27
<212> TYPE: DNA
<213> ORGANISM: Artificial Sequence

```
<220> FEATURE:
<223> OTHER INFORMATION: primer

<400> SEQUENCE: 41
ttcgtgctgt cgagcagagg gcatatc                                           27

<210> SEQ ID NO 42
<211> LENGTH: 27
<212> TYPE: DNA
<213> ORGANISM: Artificial Sequence
<220> FEATURE:
<223> OTHER INFORMATION: primer

<400> SEQUENCE: 42
gatatgccct ctgctcgaca gcacgaa                                           27

<210> SEQ ID NO 43
<211> LENGTH: 32
<212> TYPE: DNA
<213> ORGANISM: Artificial Sequence
<220> FEATURE:
<223> OTHER INFORMATION: primer

<400> SEQUENCE: 43
agacatatgc aagtaccttg ccgacatcta tg                                     32

<210> SEQ ID NO 44
<211> LENGTH: 36
<212> TYPE: DNA
<213> ORGANISM: Artificial Sequence
<220> FEATURE:
<223> OTHER INFORMATION: primer

<400> SEQUENCE: 44
gatgacaacg tcagtcatga tttgattgtc tctctg                                 36

<210> SEQ ID NO 45
<211> LENGTH: 36
<212> TYPE: DNA
<213> ORGANISM: Artificial Sequence
<220> FEATURE:
<223> OTHER INFORMATION: primer

<400> SEQUENCE: 45
cagagagaca atcaaatcat gactgacgtt gtcatc                                 36

<210> SEQ ID NO 46
<211> LENGTH: 20
<212> TYPE: DNA
<213> ORGANISM: Artificial Sequence
<220> FEATURE:
<223> OTHER INFORMATION: primer

<400> SEQUENCE: 46
gcaggtcagc ccatatgcag                                                   20

<210> SEQ ID NO 47
<211> LENGTH: 1677
<212> TYPE: DNA
<213> ORGANISM: Artificial Sequence
<220> FEATURE:
<223> OTHER INFORMATION: pPs619C1-335-540 (1537bp - 3213bp, direct)

<400> SEQUENCE: 47
atgagtaaca agagtaacga tgagttgaag tatcaagcct ctgaaaacac cttggggctt       60
aatcctgtcg ttgggctgcg tggaaaggat ctactggctt ctgctcgaat ggtgcttagg      120
```

-continued

```
caggccatca agcaaccggt gcacagcgtc aaacatgtcg cgcactttgg tcttgaactc      180
aagaacgtac tgctgggtaa atccgggctg caaccgacca gcgatgaccg tcgcttcgcc      240
gatccggcct ggagccagaa cccgctctat aaacgttatt tgcaaaccta cctggcgtgg      300
cgcaaggaac tccacgactg gatcgatgaa agtaacctcg cccccaagga tgtggcgcgt      360
gggcacttcg tgatcaacct catgaccgat gcgatggcgc cgaccaacac cgcggccaac      420
ccggcggcag tcaaacgctt ttttgaaacc ggtggcaaaa gcctgctcga cggcctctcg      480
cacctggcca aggatctggt acacaacggc ggcatgccga gccaggtcaa catgggtgca      540
ttcgaggtcg gcaagagcct gggcgtgacc gaaggcgcgg tggtgtttcg caacgatgtg      600
ctggaactga tccagtacaa gccgaccacc gagcaggtat acgaacgccc gctgctggtg      660
gtgccgccgc agatcaacaa gttctacgtt ttcgacctga gcccggacaa gagcctggcg      720
cggttctgcc tgcgcaacaa cgtgcaaacg ttcatcgtca gctggcgaaa tcccaccaag      780
gaacagcgag agtgggggcct gtcgacctac atcgaagccc tcaaggaagc ggttgacgtc      840
gttaccgcga tcaccggcag caaagacgtg aacatgctcg gggcctgctc cggcggcatc      900
acttgcactg cgctgctggg ccattacgcg gcgattggcg aaaacaaggt caacgccctg      960
accttgctgg tgaccgtgct tgataccacc ctcgacagcg acgtcgccct gttcgtcaat     1020
gaacagaccc ttgaagccgc caagcgccac tcgtaccagg ccggcgtact ggaaggccgc     1080
gacatggcga aggtcttcgc ctggatgcgc cccaacgatc tgatctggaa ctactgggtc     1140
aacaattacc tgctaggcaa cgaaccgccg gtgttcgaca tcctgttctg gaacaacgac     1200
accacacggt tgcccgcggc gttccacggc gacatgatcg aactgttcaa aaataaccca     1260
ctgattcgcc cgaatgcact ggaagtgtgc ggcaccccca tcgacctcaa gcaggtgacg     1320
gccgacatct tttccctggc cggcaccaac gaccacatca ccccgtggaa gtcctgctac     1380
aagtcggcgc aactgtttgg cggcaacgtt gaattcgtgc tgtcgagcgg cgggcatatc     1440
atgagcatcc tgaacccgcc gggcaatccg aaatcgcgct acatgaccag caccgaagtg     1500
gcggaaaatg ccgatgaatg gcaagcgaat gccaccaagc atacagattc ctggtggctg     1560
cactggcagg cctggcaggc ccaacgctcg ggcgagctga aaaagtcccc gacaaaactg     1620
ggcagcaagg cgtatccggc aggtgaagcg gcgccaggca cgtacgtgca cgaacgg       1677
```